United States Patent [19]

Poist

[11] 4,155,939
[45] May 22, 1979

[54] HYDROFORMYLATION PROCESS

[75] Inventor: John E. Poist, High Bridge, N.J.

[73] Assignee: Celanese Corporation, New York, N.Y.

[21] Appl. No.: 853,426

[22] Filed: Nov. 21, 1977

Related U.S. Application Data

[62] Division of Ser. No. 794,780, May 9, 1977, Pat. No. 4,101,565.

[51] Int. Cl.² ............................................. C07C 45/08
[52] U.S. Cl. ............................................ 260/604 HF
[58] Field of Search ................. 260/604 HF, 632 HF; 568/909

[56] References Cited

U.S. PATENT DOCUMENTS

| | | | |
|---|---|---|---|
| 3,501,531 | 3/1970 | Wilkinson | 260/604 HF |
| 3,876,672 | 4/1975 | Mrowca | 260/604 HF |
| 3,981,925 | 9/1976 | Schwager et al. | 260/604 HF |

Primary Examiner—Werren B. Lone

[57] ABSTRACT

This invention provides a novel hydroformylation catalyst which is a ligand stabilized complex of platinum dihalide dimer and stannous halide.

A preferred species of the invention hydroformylation catalyst can be represented by a formula corresponding to the chemical structure:

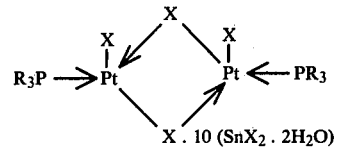

wherein R is an organic radical such as alkyl or aryl, and X is a halogen radical.

6 Claims, No Drawings

HYDROFORMYLATION PROCESS

This is a division of application Ser. No. 794,780, now U.S. Pat. No. 4,101,565, filed May 9, 1977.

BACKGROUND OF THE INVENTION

The hydroformylation reaction is employed on a commercial scale to prepare straight chain and branched chain mixtures of aldehydes and alcohols from olefinically unsaturated hydrocarbons.

For reasons of economic feasibility, improvements in hydroformylation catalysts and procedures are being investigated to achieve increased hydroformylation reaction rates and conversions, and increased selectivity to specific hydroformylation products.

The selective production of straight chain aldehydes and alcohols is particularly desirable. Higher oxo alcohols have become important intermediates for synthesis of biodegradable surface-active agents. Oxo alcohols are highly biodegradable, but the biodegradability is inversely proportional to the proportion of branched chain isomer present in an oxo alcohol mixture. There is continuing development effort to increase alpha-olefin hydroformylation selectivity to linear paraffinic aldehydes and alcohols.

Cobalt carbonyl is a conventional catalyst employed for hydroformylation reaction, but large quantities of branched chain aldehydes are produced with this catalyst. Rhodium carbonyl complexes containing tertiary phosphine or phosphite ligands [Evans et al, J. Chem. Soc. A, 3133 (1968); Pruett and Smith, J. Org. Chem., 34, 327 (1969)] are useful at low pressures and give higher ratios of straight chain to branched chain products. Similar cobalt carbonyl complexes [Slaugh and Mullineaux, J. Organometal. Chem., 13, 469 (1968)] also give more straight chain product, but produce alcohols as the primary products.

More recently developed hydroformylation catalysts and processes achieve some improved selectivity to linear products but still result in a high yield of branched chain aldehyde and alcohol products. Illustrative of recent advances in hydroformylation technology are U.S. Pat. Nos. 3,488,296; 3,652,676; 3,876,672; 3,981,925; and 3,984,486.

U.S. Pat. No. 3,981,925 is particularly pertinent with respect to improved hydroformylation selectivity. The said patent discloses a process for hydroformylation of olefins to aldehydes in the presence of a ligand stabilized platinum halide complex in combination with a Group IVA metal halide. The hydroformylation selectivity of the U.S. Pat. No. 3,981,925 process favors formation of straight chain aldehyde, e.g., in Example 1 the mole ratio of 1-octylaldehyde to 2-methylheptaldehyde product from heptene-1 hydroformylation is 9:1. Also produced are 2.7 mole percent of heptene-2 and heptene-3 isomerization products. A high pressure of carbon monoxide is required to suppress olefin isomerization.

There remains a need for hydroformylation catalysts and processes which provide for olefin conversion to aldehyde products with improved efficiency and selectivity at lower carbon monoxide pressures, and with a concomitant reduction in the yield of isomerization, hydrogenation, and polymerization products.

Accordingly, it is a main of this invention to provide a novel hydroformylation catalyst which promotes the conversion of olefins to aldehydes with a high rate of reaction and a high level of conversion.

It is a further object of this invention to provide an improved hydroformylation process for converting alpha-olefins to linear aldehydes with improved efficiency and selectivity.

Other objects and advantages of the present invention shall become apparent from the accompanying description and examples.

DESCRIPTION OF THE INVENTION

One or more objects of the present invention are accomplished by the provision of a hydroformylation process for converting olefins to aldehydes with a high reaction rate and a high molar conversion which comprises contacting an olefin with hydrogen and carbon monoxide at a temperature between about 25° C. and 125° C. and a pressure between about 50 and 3000 psi in the presence of a novel platinum dimer complex hydroformylation catalyst which corresponds to the formula:

$$[L \rightarrow PtX_2]_2 \cdot m(SnX_2)$$

wherein X is a halogen radical selected from chlorine, bromine and iodine; m is an integer between two and about twenty; and L is a monodentate ligand having the formula:

$$R_3M$$

wherein R is an organic radical selected from alkyl, alkoxyl, aryl and aryloxy groups containing between one and about twenty carbonn atoms; and M is a Group VA element selected from phosphorus, arsenic, antimony and bismuth.

The invention process is contemplated for hydroformylation of olefins containing between about 2 and 30 carbon atoms. The term olefin is meant to include substituted olefinically unsaturated compounds such as styrene. The invention process provides particular advantages in the hydroformylation of linear alkene-1 hydrocarbons containing between about 3 and 20 carbon atoms. Illustrative of linear alkene-1 compounds are propene-1, butene-1, pentene-1, hexene-1, heptene-1, decene-1, undecene-1, eicosene-1, and the like.

Hydroformylation Catalyst

The preferred catalyst for the practice of the invention hydroformylation process nominally can be represented by the structural formula:

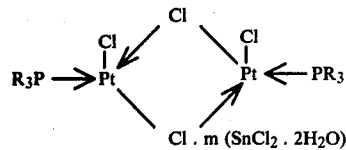

wherein R is an organic radical selected from alkyl, alkoxyl, aryl and aryloxy substituents containing between one and about twenty carbon atoms; and m is an integer between two and about twenty.

The catalyst can be employed in a quantity which is in a molar ratio of about one mole of catalyst per 20–1000 moles of olefin feed being hydroformylated. An average molar ratio of 1 mole of catalyst per 100–500 moles of olefin is generally a preferred range.

An important aspect of the present invention catalyst is the relative quantities of catalyst components provided in the hydroformylation medium.

The stannous halide component is provided in a molar ratio between about 2-50 moles, and preferably between about 2-20 moles, per mole of platinum dihalide dimer component in the hydroformylation medium. A highly preferred stannous halide component is stannous chloride dihydrate. The dihydrate form of stannous chloride promotes a faster olefin hydroformylation reaction rate and a higher level of olefin conversion than does anhydrous stannous chloride.

The monodentate ligand component is complexed in the platinum dihalide dimer catalyst in a molar ratio of 1:1 with respect to the platinum dihalide content of the catalyst.

It is a further embodiment of the present invention process that the monodentate ligand is incorporated in the hydroformylation medium in a molar excess, i.e., a quantity of ligand which is in molar excess over that required to complex and stabilize the platinum dihalide component of the catalyst system. The catalyst complex and excess ligand can be represented as follows:

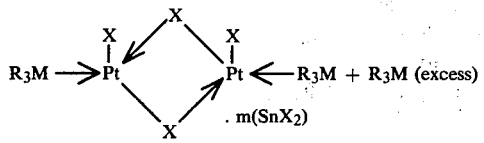

wherein R, M, m, and X are as defined hereinabove.

The presence of excess ligand in the olefin hydroformylation system is important for the achievement of highly selective production of straight chain aldehydes from α-olefins in a normal/iso molar ratio of at least 9 to 1. The excess ligand can be the same or different than the ligand present in the ligand stabilized platinum dihalide dimer complex. The quantity of excess ligand can average in the range between about 1-100 moles per mole of platinum dihalide dimer complex in the hydroformylation system.

Illustrative of suitable catalyst ligands are the following compounds:

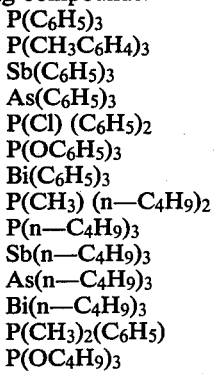

As demonstrated in EXAMPLE II of the present disclosure, in the absence of excess ligand in the hydroformylation medium the α-olefin feed converts to aldehydic product in a normal/iso molar ratio of about 5.6 to 1. This is to be compared with the results reported in EXAMPLE III, wherein the molar ratio of normal/iso aldehyde product is 9.3 to 1.

Hydroformylation Conditions

As a general procedure, the catalyst system is first formed in a deoxygenated solvent medium in a hydroformylation reaction zone. Excess ligand can perform as the solvent medium. The hydroformylation zone is pressured with hydrogen and carbon monoxide and heated to a selected reaction temperature. Olefin feed is then charged to the hydroformylation zone, and the reaction is conducted until the desired conversion yield and efficiency have been attained.

It is preferred that the temperature of the hydroformylation reaction be maintained in the range between about 25° C. and 125° C. For most of the olefin oxonation reactions, a reaction temperature between about 50° C. and 110° C. and a reaction time between about 2 and 5 hours are particularly preferred.

The pressure in the hydroformylation reaction zone can vary over a range between about 50-3000 psi. Preferred pressures are those in the range between about 100-1500 psi, particularly for the selective hydroformylation of alpha-olefins to linear aldehydes.

The ratio of hydrogen to carbon monoxide can vary broadly over a mole ratio range between about 30:1 and 1:30. The average mole ratio will vary between about 10:1 and 1:10. The quantity of hydrogen/carbon monoxide charged should be at least sufficient to satisfy the stoichiometric requirements of the olefin hydroformylation system.

Although it is not essential, an inert solvent can be employed as a hydroformylation reaction medium diluent. A variety of solvents can be used including ketones such as acetone, methyl ethyl ketone, methyl isobutyl ketone, acetophenone, and cyclohexanone; aromatics such as benzene, toluene and xylenes; halogenated aromatics including orthodichlorobenzene; ethers such as tetrahydrofuran, dimethoxyethane and dioxane; halogenated paraffins including methylene chloride; paraffinic hydrocarbons such as heptane; and the like.

The present invention olefin hydroformylation process is characterized by a faster hydroformylation reaction rate and a higher level of olefin conversion than prior art processes employing a platinum catalyst. Hence, in EXAMPLE I of the present disclosure in accordance with the hydroformylation procedure and catalyst of U.S. Pat. No. 3,981,925, 84 percent of the olefin feed was converted to 95 mole percent of aldehydes in 180 minutes. In EXAMPLE III in accordance with the present invention process, 99 percent of the olefin feed was converted to 92 mole percent of aldehydes in 110 minutes.

The following examples are illustrative of specific embodiments of the present invention process. As it is apparent to those skilled in the art, in the light of the foregoing disclosure numerous modifications are possible in the practice of the invention process without departing from the scope or concept thereof.

EXAMPLE I

This Example illustrates the hydroformylation of hexene-1 in the presence of a prior art platinum catalyst complex.

In a manner similar to that described in U.S. Pat. No. 3,981,925, to a 300 milliliter magnadrive autoclave was added a solution of 58.5 milliliters of methyl isobutyl ketone and 0.325 gram of stannous chloride dihydrate under a nitrogen atmosphere. After 15 minutes, 0.229 gram of triphenylphosphine-platinum dichloride complex was added with stirring.

The autoclave was pressured with 1500 psig $H_2/CO$ (1:1) and heated to 78° C. A solution of 4.88 milliliters of hexene-1 and 2.9 milliliters of benzene were charged to the autoclave, and the hydroformylation was commenced.

The hydroformylation reaction was conducted at 78°-80° C. for 180 minutes. The reactor was cooled, and the contents were analyzed by gas chromatography. The analytical data indicated that 84 perlcent of the hexene-1 feed had converted to 95 mole percent of heptanal-1 and 2-methylhexanal-1. The aldehyde molar ratio of heptanal-1 to 2-methylhexanal-1 was 11.4 to 1.

EXAMPLE II

This Example illustrates the hydroformylation of hexene-1 in the presence of a present invention platinum dihalide dimer complex catalyst.

In a manner similar to that described in EXAMPLE I, an autoclave was charged with 52 milliliters of methyl ethyl ketone and 0.325 gram of stannous chloride dihydrate, and then with 0.120 gram of tri(n-butyl)phosphine stabilized platinum dichloride dimer complex:

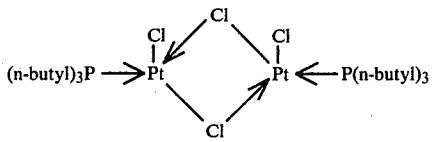

The autoclave was pressured with 1500 psig $H_2/CO$ (1:1) and heated to 81° C. A solution of 4.88 milliliters of hexene-1 and 0.88 milliliters of benzene were charged to the autoclave, and the hydroformylation reaction was conducted at 81°-82° C. for 85 minutes.

The reactor was cooled, and analytical data indicated that 94 percent of the hexene-1 feed had converted to 94 mole percent of heptanal-1 and 2-methylhexanal-1. The aldehyde molar ratio of heptanal-1 to 2-methylhexanal-1 was 5.6.

EXAMPLE III

This Example illustrates the hydroformylation of hexene-1 in the presence of a present invention platinum dihalide dimer complex catalyst and a molar excess of phosphine ligand.

In a manner similar to that described in EXAMPLE I, an autoclave was charged with 52 milliliters of methyl ethyl ketone and 0.325 gram stannous chloride dihydrate, and then with 0.76 gram of triphenylphosphine and 0.136 gram of tri(n-butyl) phosphine stabilized platinum dichloride dimer complex. The quantity of triphenylphosphine ligand was in a one mole excess per mole of platinum dimer complex.

The autoclave was pressured with 1500 psig $H_2/CO$ (1:1), and heated to 78° C. A solution of 4.88 milliliters of hexene-1 and 0.88 milliliters of benzene were charged to the autoclave, and the hydroformylation reaction was conduted at 78° C. for 110 minutes.

The reactor was cooled, and analytical data indicated that 99 percent of the hexene-1 had been converted to 92 mole percent of heptanal-1 and 2-methylhexanal-1. The aldehyde molar ratio of heptanal-1 to 2-methylhexanal-1 was 9.3 to 1.

What is claimed is:

1. A process for the preparation of alkanal-1 by hydroformylation of an alpha-olefin containing between about 2 and 30 carbon atoms with a high reaction rate and a high molar conversion which comprises contacting an alpha-olefin with hydrogen and carbon monoxide at a temperature between about 25° C. and 125° C. and a pressure between about 50 and 3000 psi in the presence of a platinum dimer complex hydroformylation catalyst which corresponds to the formula:

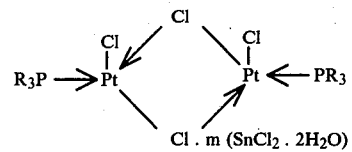

$Cl \cdot m \, (SnCl_2 \cdot 2H_2O)$ wherein R is an organic radical selected from alkyl, alkoxyl, aryl and aryloxy groups containing between one and about twenty carbon atoms; and m is an integer between two and about twenty.

2. A hydroformylation process in accordance with claim 1 wherein the R radical is phenyl in the formula.

3. A hydroformylation process in accordance with claim 1 wherein the R radical is butyl in the formula.

4. A hydroformylation process in accordance with claim 1 wherein the alpha-olefin is styrene.

5. A hydroformylation process in accordance with claim 1 wherein the alpha-olefin is a linear alkene-1 hydrocarbon containing between three and about twenty carbon atoms.

6. A hydroformylation process in accordance with claim 5 wherein the linear alkene-1 hydrocarbon is hexene-1.

* * * * *